US00PP17828P2

(12) United States Plant Patent
Zaiger et al.

(10) Patent No.: US PP17,828 P2
(45) Date of Patent: Jun. 26, 2007

(54) INTERSPECIFIC TREE NAMED 'CANDY STRIPE'

(50) Latin Name: [*(Prunus salicina×(Prunus salicina×Prunus armeniaca))×Prunus salicina*]
Varietal Denomination: Candy Stripe

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 24 days.

(21) Appl. No.: 11/294,197

(22) Filed: Dec. 6, 2005

(51) Int. Cl.
*A01H 5/00* (2006.01)

(52) U.S. Cl. ..... Plt./180
(58) Field of Classification Search ..... Plt./180, Plt./190, 184
See application file for complete search history.

*Primary Examiner*—Kent Bell
*Assistant Examiner*—Annette H Para

(57) ABSTRACT

A new and distinct variety of interspecific tree. The following features of the tree and its fruit are characterized with the tree budded on 'Citation' Rootstock (U.S. Plant Pat. No. 5,112), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of fruit.
2. Fruit with excellent flavor and eating quality.
3. Fruit holding firm on the tree 3 weeks after maturity (shipping ripe).
4. Relatively uniform size fruit throughout the tree.
5. Fruit with good handling and storage quality.
6. Fruit with a good balance between acid and sugar with an average Brix of 16.3°.

1 Drawing Sheet

Botanical classification: [(*Prunus salicina*×(*Prunus salicina*×*Prunus armeniaca*))×*Prunus salicina*].

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plums, which are known to us, and mentioned herein, 'Autumn Giant' Plum (U.S. Plant Pat. No. 5,624) and 'King David' Plum (non-patented).

ORIGIN OF THE VARIETY

The present new variety of interspecific tree [(plum× plumcot)×plum] was developed by us in our experimental orchard located near Modesto, Calif., as a first generation cross of proprietary parent '25EB128' with 'Autumn Giant' Plum (U.S. Plant Pat. No. 5,624). The maternal parent (25EB128) originated from a cross between 'King David' Plum (non-patented) and the proprietary plumcot '4G1180'. A large number of seedlings from this first generation cross were planted and grown on their own root. Under close and careful observation, one such seedling exhibited desirable tree and fruit characteristics and was selected in 1989 for additional asexual propagation and commercialization.

ASEXUAL REPRODUCTION OF THE VARIETY

Asexual reproduction of the new and distinct variety of interspecific tree was by budding to '4-G-816' Rootstock (U.S. Plant Pat. No. 5,112), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of interspecific tree [(*Prunus salicina*× (*Prunus salicina*×*Prunus armeniaca*))×*Prunus salicina*] is of large size, vigorous, upright growth and a productive and regular bearer of medium size, clingstone fruit with excellent flavor and eating quality. The fruit remains firm on the tree approximately 21 days after maturity (shipping ripe) and is relatively uniform in size and maturity throughout the tree. The fruit is nearly globose in shape with an attractive yellow-orange skin color. In comparison to its maternal parent (25EB128), the fruit of the new variety is larger in size, yellow-red in skin color compared to red and is approximately 35 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 7 years of age, its flowers, foliage and fruit, as based on observations of 7 year old specimens grown near Modesto, Calif., with color in accordance with Munsell Book of Color.

Tree:

*Size.*—Large, usually pruned to approximately 3.5 meters in height for economical harvesting of fruit. Average spread 3 meters, varies with different cultural practices.

*Vigor.*—Vigorous, growth of 1.5 to 2 meters in height the first growing season, varies with soil type, fertility, climatic conditions and cultural practices.

*Form.*—Upright, usually pruned to vase shape.

*Branching habit.*—Upright, crotch angle approximately 30°, increases with heavy crop load.

*Productivity.*—Productive, thinning and spacing of fruit necessary for desirable market size fruit.

*Bearer.*—Regular, adequate fruit set 5 consecutive years, no alternate bearing observed.

*Fertility.*—Self sterile, pollinator required.

*Density.*—Medium dense, usually pruned to vase shape to allow more sunlight to center of tree to enhance fruit color and health of fruit spurs.

*Hardiness.*—Tree grown in USDA Hardiness Zone 9. Hardy in all stone fruit growing areas of California. Winter chilling requirement approximately 450 to 500 hours at or below 45° F.

Trunk:

*Size.*—Large. Average circumference 50.8 cm at 21.5 cm above ground on a 7 year old tree.

*Texture.*—Medium shaggy, increases with age of tree.

*Color.*—Varies from 10YR 5/2 to 5YR 7/2.

Branches:

*Size.*—Medium. Average circumference 15.7 cm at 1 meter above ground.

*Surface texture.*—New growth relatively smooth. Mature growth medium rough, roughness increases with age.

*Lenticels.*—Large. Average number 37 in a 25.8 sq cm surface. Average length 4.36 mm. Average width 1.24 mm. Color varies from 2.5YR 6/12 to 2.5YR 5/8.

*Color.*—New growth varies from 2.5GY 6/8 to 2.5GY 6/6. Old growth varies from 7.5YR 3/4 to 7.5YR 3/6, varies with age of growth.

Leaves:

*Size.*—Medium. Average length 96 mm. Average width 43.7 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 13.1 mm. Average width 1.3 mm. Longitudinally grooved. Surface — glabrous. Color varies from 5GY 7/6 to 7.5GY 8/8.

*Glands.*—Type — globose. Size — small. Average length 0.6 mm. Average diameter 0.3 mm. Average number 2, varies from 1 to 3. Located on upper portion of petiole and lower portion of leaf blade. Color varies from 7.5GY 8/6 to 5GY 7/6.

*Color.*—Upper surface varies from 7.5GY 4/4 to 5GY 3/4. Lower surface varies from 7.5GY 6/4 to 5GY 5/4. Midvein color 5GY 9/4.

Flower buds:

*Size.*—Small to medium. Average length 7.8 mm. Average diameter 4.8 mm.

*Hardiness.*—Hardy in all stone fruit growing areas of California.

*Form.*—Conical, becoming slightly elongated just before opening.

*Pedicle.*—Surface — glabrous. Average length 9.3 mm. Average width 0.63 mm. Color varies from 5GY 7/6 to 5GY 8/6.

*Color.*—N 9/0.5 (white).

*Number of buds per spur.*—Average number 8, varies from 2 to 14.

Flowers:

*Size.*—Medium. Average height 9.9 mm. Average diameter 19.0 mm.

*Petals.*—Number 5, alternately arranged to sepals. Form — obovate, narrows at point of attachment. Size — small to medium. Average length 9.7 mm. Average width 8.3 mm. Margin — sinuate. Both surfaces glabrous. Color N 9/0.5 (white).

*Sepals.*—Number 5, alternately arranged to petals. Shape — triangular, apex rounded. Both surfaces glabrous. Size — small. Average length 2.7 mm. Average width 2.0 mm. Color — upper surface varies from 2.5GY 5/8 to 5GY 6/8. Lower surfaces varies from 2.5GY5/6 to 5GY 6/8.

*Stamens.*—Average number per flower 30. Average filament length 9.8 mm. Filament color N 9/0.5 (white). Anther color varies from 2.5Y 8/10 to 5Y 8/12.

*Pollen.*—Self sterile, pollinator required. Color varies from 2.5Y 7/10 to 5Y 8/12.

*Pistil.*—Number — normally one. Surface glabrous. Average length 8.6 mm. Position of stigma average of 1.3 mm below anthers. Color varies from 2.5GY 8/6 to 5GY 9/4.

*Fragrance.*—Slight.

*Blooming period.*—Date of First Bloom Feb. 24, 2005. Date of Petal Fall Mar. 6, 2005, varies slightly with climatic conditions.

*Color.*—N 9/0.5 (white).

*Number flowers per flower bud.*—Usually 3, varies from 1 to 4.

*Pedicel.*—Average length 10.4 mm. Average width 0.6 mm. Color varies from 5GY 7/6 to 5GY 8/8.

Fruit:

*Maturity when described.*—Firm ripe.

*Date of first picking.*—Jul. 19, 2005.

*Date of last picking.*—Jul. 26, 2005, varies slightly with climatic conditions.

*Size.*—Medium. Average diameter axially 64.2 mm. Average transversely in suture plane 60.5 mm. Average weight 121.5 grams, varies slightly with fertility of the soil, amount of thinning and climatic conditions.

*Form.*—Globose.

*Suture.*—Very slightly lipped, nearly smooth, extends from base to apex.

*Ventral surface.*—Slightly lipped, relatively smooth.

*Apex.*—Nearly rounded.

*Base.*—Varies from flat to nearly rounded.

*Cavity.*—Rounded to slightly elongated in suture plane. Average depth 4.5 mm. Average diameter 6.0 mm.

Stem:

*Size.*—Medium. Average length 16.0 mm. Average diameter 2.2 mm.

*Color.*—Varies from 10Y 7/4 to 10Y 7/6.

Flesh:

*Ripens.*—Evenly.

*Texture.*—Firm, meaty.

*Fibers.*—Few, small, tender.

*Firmness.*—Firm, comparable to 'Autumn Giant' Plum (U.S. Plant Pat. No. 5,624).

*Aroma.*—Slight.

*Amydgalin.*—Undetected.

*Eating quality.*—Excellent.

*Flavor.*—Excellent, good balance between acid and sugar.

*Juice.*—Moderate, enhances flavor.

*Brix.*—Average 16.3°, varies slightly with amount of fruit per tree and climatic conditions.

*Color.*—Varies from 2.5Y 8.5/6 to 2.5Y 8/8. Pit cavity varies from 2.5Y 7/12 to 2.5Y 6/10.

Skin:

*Thickness.*—Medium.

*Surface.*—Smooth.

*Bloom.*—Moderate, complete coverage.

*Tendency to crack.*—None.

*Color.*—Ground color varies from 5Y 8.5/8 to 5Y 8.5/10. 50% overspread with 7.5R 4/10 to 7.5R 4/14. Very small, randomly spaced areas of ground cover exposed to surface creating a speckling pattern to skin in some areas.

*Tenacity.*—Tenacious to flesh.

*Astringency.*—None.

Stone:

*Type.*—Clingstone.

*Size.*—Medium. Average length 23.8 mm. Average width 17.8 mm. Average thickness 8.8 mm.

*Form.*—Obovoid.

*Base.*—Usually flat, varies from flat to rounded.

*Apex.*—Pointed. Average length 0.9 mm.

*Surface.*—Lightly pitted throughout, one small groove on each side of suture extending from base to apex.

*Sides.*—Varies from equal to unequal with one side extending further from suture plane.

*Ridges.*—One long small ridge created by groove, several small short ridges extending from base toward apex.

*Tendency to split.*—None.

*Color.*—Varies from 5YR 8/4 to 5YR 7/8 when dry.

Kernal:

*Form.*—Ovate.

*Taste.*—Bitter.

*Viability.*—Viable, complete embryo.

*Size.*—Small. Average length 12.8 mm. Average width 9.0 mm. Average thickness 5.8 mm.

*Skin.*—Color varies from 5YR 6/6 to 5YR 6/8.

Use: Dessert. Market — local and long distance.

Keeping quality: Good, stored 3 weeks at 38° to 42° F. without internal breakdown of flesh or appreciable loss of flavor.

Shipping quality: Good, minimal skin scarring or flesh bruising during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a regular and productive bearer of medium size, clingstone fruit with firm flesh, excellent flavor and eating quality; the fruit is further characterized by holding firm on the tree three weeks after maturity (shipping ripe), is relatively uniform in size throughout the tree, has an attractive yellow-red skin color with the flesh having a good balance between acid and sugar.

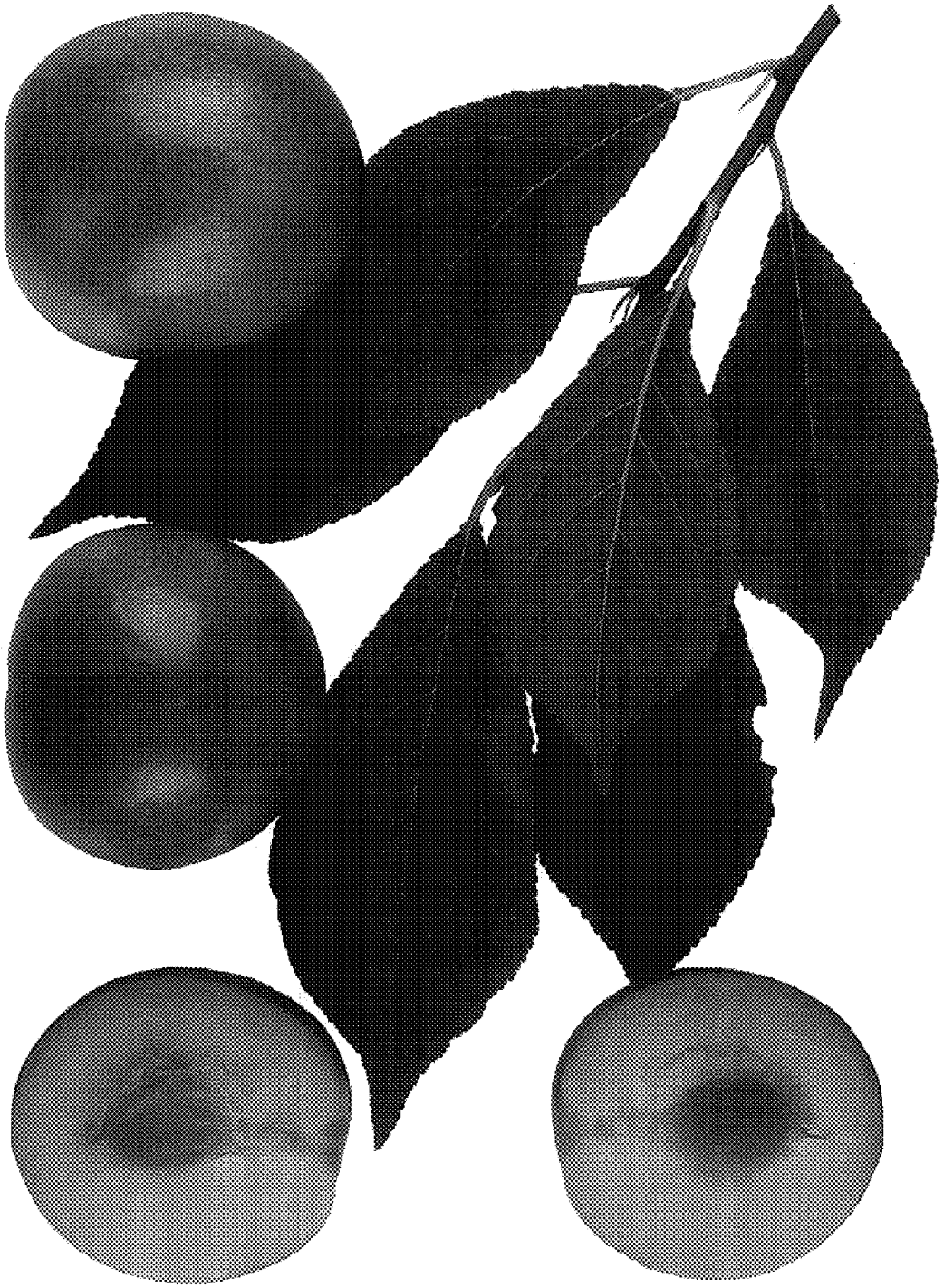

* * * * *